United States Patent [19]

Strawder

[11] Patent Number: 5,226,068
[45] Date of Patent: Jul. 6, 1993

[54] HOLDER FOR X-RAY CASSETTES

[76] Inventor: Glenn G. Strawder, Apt. 507, 11800 Beltsville Dr., Beltsville, Md. 20705

[21] Appl. No.: 820,075

[22] Filed: Jan. 13, 1992

[51] Int. Cl.⁵ .................. G03B 42/04; G03B 41/16
[52] U.S. Cl. ................................ 378/177; 378/167; 378/208
[58] Field of Search ............. 378/167, 170, 177, 178, 378/179, 180, 204, 205, 208

[56] References Cited

U.S. PATENT DOCUMENTS

| | | | |
|---|---|---|---|
| 2,478,597 | 8/1949 | Scarpellino | 378/177 |
| 3,293,430 | 12/1966 | Wustner | 378/177 |
| 3,916,207 | 10/1975 | Reed | 378/177 |
| 4,352,197 | 9/1982 | Waerve | 378/177 |
| 4,414,683 | 11/1983 | Robinson | 378/177 |
| 4,700,373 | 10/1987 | Miller | 378/177 |
| 5,133,000 | 7/1992 | Möller | 378/177 |

Primary Examiner—David P. Porta
Attorney, Agent, or Firm—William D. Hall

[57] ABSTRACT

An X-ray cassette holder having a vertical cavity for receiving a cassette and positioning the cassette vertically next to a patient. The holder also provides a ramp for permitting an injured patent to be positioned on a raised flat portion of the device adjacent the vertical cassette.

19 Claims, 2 Drawing Sheets

HOLDER FOR X-RAY CASSETTES

BACKGROUND OF THE INVENTION

This invention relates to a device for holding an x-ray film cassette while an x-ray of a part of the body of either a human being or of an animal is being taken.

In the practice of emergency medicine it is frequently necessary to make an x-ray of a part of a human body that has been seriously injured and cannot move in response to the requests of an x-ray technician who has been asked to take an x-ray. Frequently, the x-ray film is in a cassette and the x-ray technician has difficultly in positioning the part of the body of the patient, that is to be x-rayed, between the source of the x-rays and the cassette that hold the film.

SUMMARY OF THE INVENTION

The apparatus of the present invention has a portable base which defines a slot or groove that holds an x-ray cassette in a vertical position even if the cassette is contacted by a part of the body of a person who is being x-rayed. The base has a raised flat portion on which the part of the body to be x-rayed is placed. The base provides a ramp in front of the flat raised portion for receiving the patient whose x-ray is to be taken.

Since the patient is often unable to respond to requests made by the x-ray technician, the ramp is especially useful. It permits the injured patient to be readily positioned in front of the cassette. This may be done by sliding the ramp under a part of a person who is on a flat surface, or by holding the base in place and sliding the patient onto the ramp on his or her way to the flat raised portion.

DETAILED DESCRIPTION OF THE INVENTION

Figure 1:
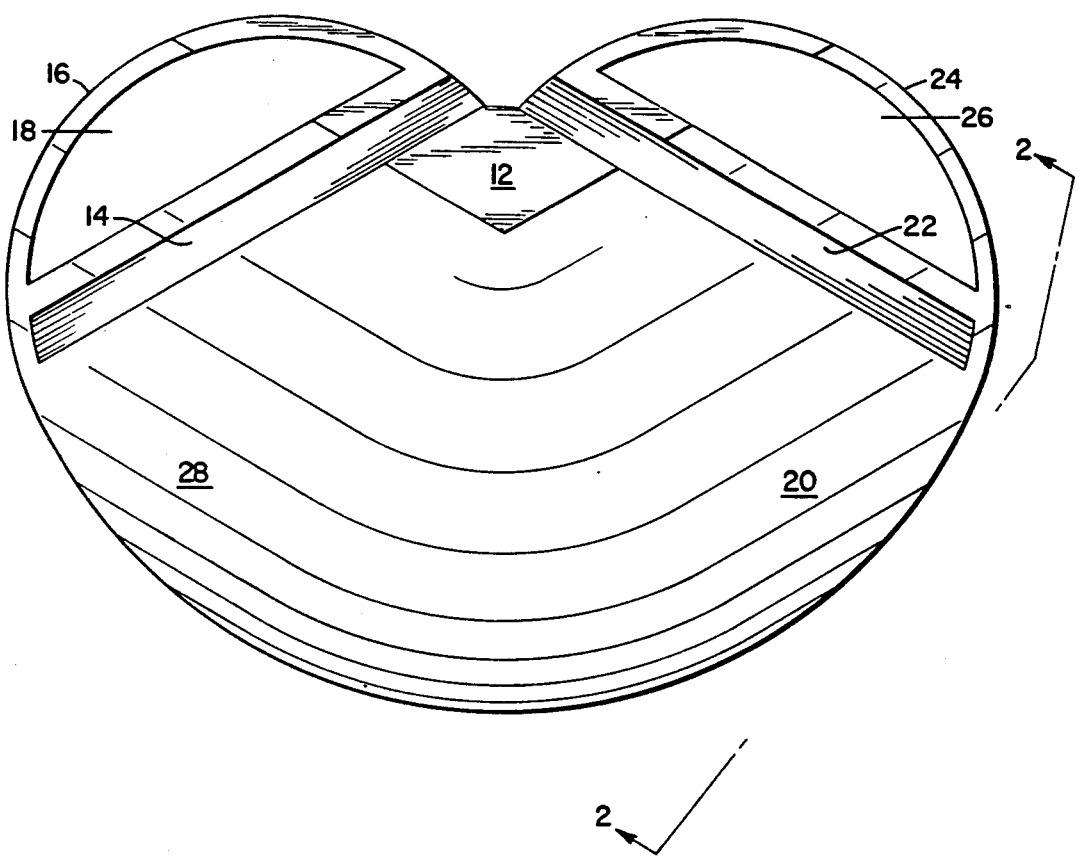
FIG. 1 is a plan view of a base which embodies my invention.
Figure 2:
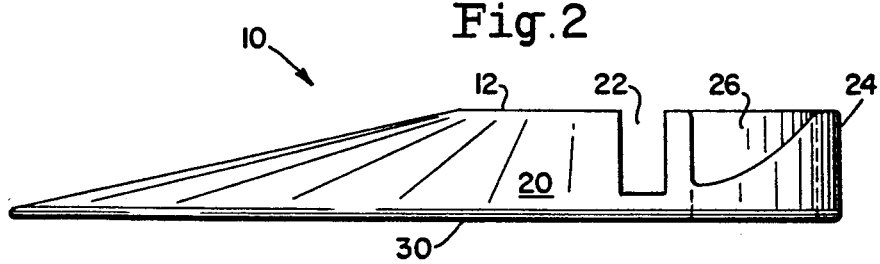
FIG. 2 is a side view of the base of FIG. 1, when viewed along line 2—2 of FIG. 1.

In FIG. 1, the base 10 has slots 14 and 22 which are as wide as the cassette is thick and are deep enough to hold, a cassette which is placed therein, tightly, so that the cassette extends upward in a vertical plane. The cassette is held so tightly that it will maintain its vertical position even if it is contacted by the patient. The base 10 has a raised flat portion 12 at the end of the ramp 20, 28. The portion, of the body, to be x-rayed is placed on the raised flat portion. The bottom surface 30 of the base 10 is smooth to permit it to readily slide on a floor or other flat surface. It may, therefore easily slide under the patient. It may be a layer of Teflon (TM). The base 10 has handles 16 and 24 adjacent to depressions 18 and 26, respectively. The handles and depressions enable the hand or hands of the technician to grab the base so that the base may be held in place, or moved under the patient, preparatory to taking the x-ray.

Figure 3:
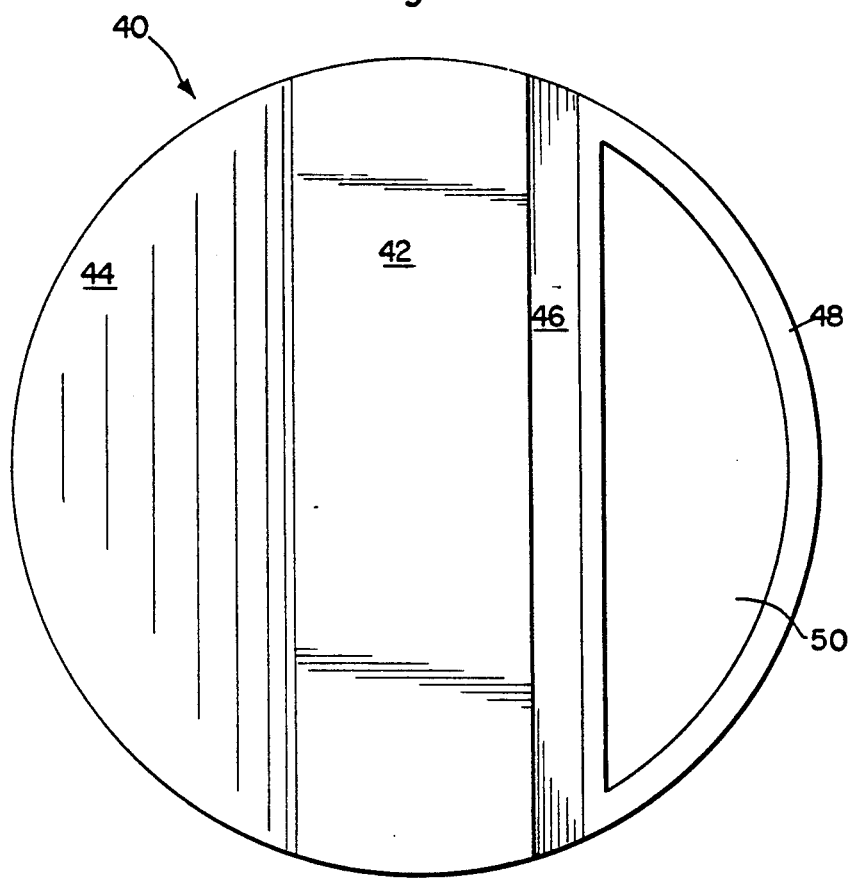
FIG. 3 is a plan view of another form of my invention.
Figure 4:
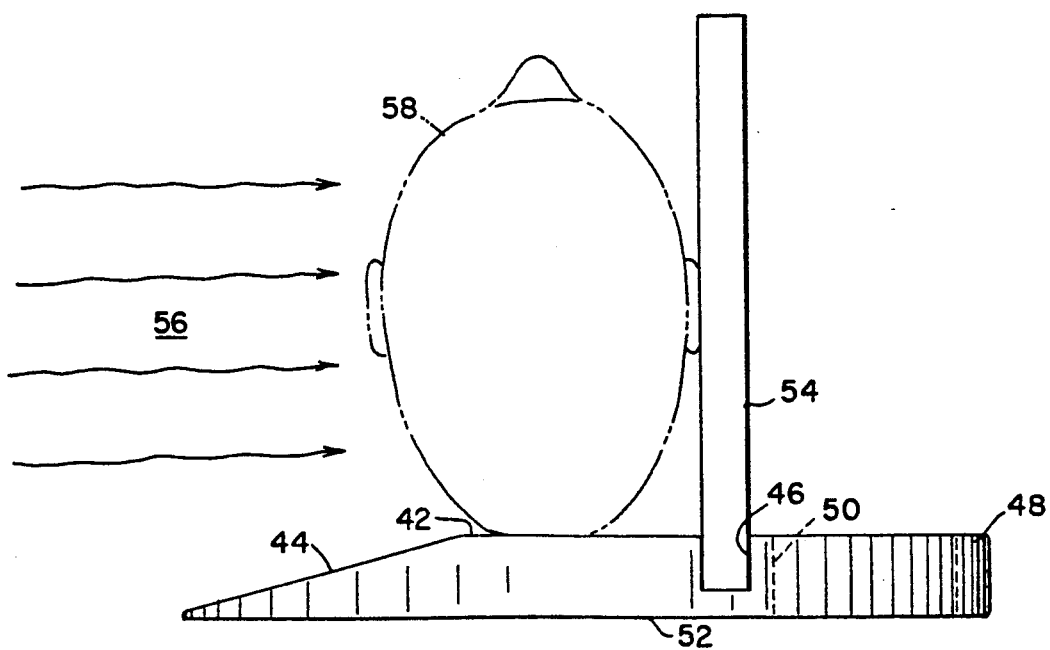
FIG. 4 is a side view of the apparatus of FIG. 3. In this figure, however, the head 58 of a human being is in a position to be x-rayed by the x-rays 56 that are directed at cassette 54.

In the modified form of FIG. 3 the base 40 has a slot 46 which has the same depth and width as the slots 14 and 22 of FIG. 1. The ramp 44 leads to the horizontal flat surface 42. The lower face 52 of base 40 is smooth to permit the base to slide into place. The rim 48 and the depression 50 form a handle that serves the same purpose as the handles 16 and 24 of FIG. 1.

With either the form of the invention of FIG. 1, or FIG. 3, the part of the body of the patient to be x-rayed is positioned on the horizontal flat surface 12 or 42, as the case may be. This may be done by sliding the patient up the ramp (20, 28, or 44) or by sliding the ramp under the patient.

The x-ray is then taken by directing the x-rays through the patient and into the cassette where the x-rays intersect the film.

The cassette may be placed in any one of the slots 14, 22 or 46 either before or after the patient is placed on the raised flat portion 12 or 42 as the case may be.

The base 10, or 40, as the case may be, may be plastic and molded in one piece, and therefore is low in cost.

I claim:

1. The method of positioning a body and a cassette, containing an x-ray film, relative to each other, to permit an x-ray to be taken, comprising:
   providing a base that defines: a bottom side, an elevated portion, a ramp extending from substantially adjacent said bottom side to said elevated portion and a vertical slot that extends downward from said elevated portion toward said bottom side for receiving said cassette,
   positioning a body and said cassette relative to each other on said elevated portion so that x-rays passing in a given path through said body will intersect and cassette, including placing said cassette in said slot, and transmitting x-rays along said path.

2. The method of claim 1, comprising:
   moving the ramp relative to the patient in order to position the body on said elevated portion.

3. The method of claim 2, comprising:
   providing said base with a handle, and
   using said handle to hold the base while the patient is positioned on the base.

4. The method of claim 2, which includes sliding the base into a position under the portion of the body of the patient to be x-rayed.

5. A device for holding an x-ray cassette, comprising:
   a body support having a bottom side, a ramp extending from substantially adjacent said bottom side to an elevated position,
   said body support comprising means for supporting at least a portion of a body on said elevated position,
   said body support defining a vertical cavity, that extends from a portion of said elevated position downward toward said bottom side, for receiving an x-ray cassette.

6. A device as defined in claim 5 in which said elevated position is relatively flat.

7. A device as defined in claim 6 in which said elevated position is horizontal.

8. A device as defined in claim 5, which is molded in one piece.

9. A device as defined in claim 5 in which said bottom side is smooth to permit the device to slide under the body.

10. A device as defined in claim 5, which defines a depression therein which permits the device to be held by a human hand.

11. A device as defined in claim 5 which is molded in one piece, in which said elevated position is a relatively flat horizontal portion.

12. A device as defined in claim 11 having a smooth bottom surface.

13. A device as defined in claim 12 in which said device has an outer surface and defines a depression adjacent said outer surface so that the portion of the device between the outer surface and the depression may be grasped by a human hand.

14. Apparatus for positioning an x-ray cassette and a portion of a body of a patient relative to each other, comprising:

a base having a slot for receiving an x-ray cassette and constituting means for holding the cassette in a desired position, so that x-rays of said portion of said body may be taken, said base having first and second slots for receiving first and second cassettes, said slots being at an angle to each other that is less than 180 degrees, said base having a raised surface in the space between said slots.

15. Apparatus as defined in claim 14, said base having a ramp extending upwardly to said raised surface, said raised surface being located between said ramp and said slots.

16. Apparatus as defined in claim 15, comprising:

said base having at least one depression that forms a handle, said depression and said surface being, on opposite sides of said slots.

17. Apparatus as defined in claim 16 having two depressions one adjacent each slot.

18. Apparatus as defined in claim 14 in which said base defines a depression that forms a handle for positioning said base relative to said portion of said body.

19. Apparatus as defined in claim 14 in which said base has a smooth bottom surface that facilitates sliding said base under the body of a patient.

* * * * *

UNITED STATES PATENT AND TRADEMARK OFFICE
CERTIFICATE OF CORRECTION

PATENT NO. : 5,226,068

DATED : July 6, 1993

INVENTOR(S) : Glenn G. Strawder

It is certified that error appears in the above-identified patent and that said Letters Patent is hereby corrected as shown below:

Column 2, line 34, claim 1, the word "and" should be --said--.

Signed and Sealed this

Eighth Day of March, 1994

BRUCE LEHMAN

Attest:

Attesting Officer

Commissioner of Patents and Trademarks